United States Patent [19]

Chiou et al.

[11] Patent Number: 5,041,450

[45] Date of Patent: Aug. 20, 1991

[54] TREATMENT OF OCULAR INFLAMMATION

[75] Inventors: George C. Y. Chiou; Ching-Yao Chuang, both of College Station, Tex.

[73] Assignee: Research Corporation Technologies, Inc., Tuscon, Ariz.

[21] Appl. No.: 213,061

[22] Filed: Jun. 29, 1988

[51] Int. Cl.$^5$ .............................................. A61K 31/44
[52] U.S. Cl. .................................... 514/288; 514/888; 514/915
[58] Field of Search ................ 514/288, 888, 915, 284

[56] References Cited

PUBLICATIONS

Polanksky et al. (1984) in *Pharmacology of the Eye* (Sears, M. L., ed) Springer-Valag, New York, pp. 459-538; Anti-Inflammatory Agents: Steroids as Anti--Inflammatory Agents.

Masuda (1984) in *Pharmacology of the Eye* (Sears, M. L., ed) Springer-Valag, New York, pp. 539-551; Anti-Inflammatory Agents: Nonsteroidal Anti-Inflammatory Drugs.

Cho et al. (1986) *Planta Medica* 5: 343-345; Study of the Antipyretic Activity of Matrine: A Lupin Alkaloid Isolated from *Sophora subprostrata*.

Cho et al. (1986) *IRCS Med. Sci.* 14, 441-442; Study of the Anti-Inflammatory Action of Matrine: An Alkaloid Isolated from *Sophora subprostrata*.

*Primary Examiner*—John W. Rollins
*Attorney, Agent, or Firm*—Scully, Scott, Murphy & Presser

[57]. ABSTRACT

The present invention contemplates a treatment for ocular inflammation.

More particularly, one aspect of the present invention relates to a method of reducing, inhibiting or preventing ocular inflammation in a mammal which comprises administering to said mammal an effective amount of matrine or a derivative thereof.

Another aspect of the present invention is directed to a pharmaceutical composition useful in reducing, inhibiting or preventing ocular inflammation in a mammal comprising an effective amount of matrine or a derivative thereof and a pharmaceutically acceptable carrier.

Yet another aspect of the present invention contemplates a method of inducing ocular analgesia and a pharmaceutical composition useful for same.

19 Claims, 3 Drawing Sheets

TREATMENT OF OCULAR INFLAMMATION

FIELD OF THE INVENTION

The present invention contemplates a method of treating ocular inflammation. More particularly, the present invention is directed to the treatment of ocular inflammation by the administration of matrine or a derivative thereof. The present invention also relates to the use of matrine and its derivatives as an ocular analgesic.

BACKGROUND OF THE INVENTION

Recent developments in surgical operations for primary cataract, narrow angle glaucoma and the like and laser treatment of retina diseases, secondary cataract and the like have resulted in ocular inflammation becoming a major problem in eye clinics. Although corticosteroids are potent and effective agents for reducing inflammation, their use is contraindicated in glaucoma and ocular hypertensive patients due to their ocular hypertensive actions (Schwartz, *Int. Ophthal. Clin.* 6:753–797, 1966; Polansky et al. *Pharmacology of the Eye* (Sears, M.L., Ed.) Springer-Verlag, New York, pp. 459–538, 1984).

Non-steroidal antiinflammatory agents have been extensively investigated in an effort to find an effective replacement for corticosteroids. Only minor success has to date been achieved (Masuda, In *Pharmacology of the Eye* (Sears, M.L., Ed.) Springer-Verlag, New York, pp. 539–552, 1984). These agents are either cyclooxygenase inhibitors to prevent prostaglandin production or lipoxygenase inhibitors to prevent leukotriene production. In general, they are much less effective than steroidal antiinflammatory agents and possess numerous untoward side effects (Masuda, *supra*).

Matrine is a natural product isolated from *Sophora subprostrata* and has been used extensively as a systemic antiinflammatory agent in China (Cho et al., *IRCS Med. Sci.* 14:441–442, 1986; *Chinese Traditional Medicine Encyclopedia*, Hsin-Wen-Fong Publishing Co., Taiwan, Vol. 1, pp. 230–232, 1985). In accordance with the present invention, it is surprisingly discovered that matrine is useful in the treatment of ocular inflammation without producing ocular hypertension. The present invention, therefore, fulfils a long felt need to provide an effective, non-steroidal agent for reducing, inhibiting or preventing ocular inflammation without untoward side effects.

SUMMARY OF THE INVENTION

The present invention contemplates a treatment for ocular inflammation.

More particularly, one aspect of the present invention relates to a method of reducing, inhibiting or preventing ocular inflammation in a mammal which comprises administering to said mammal an effective amount of matrine or a derivative thereof for a time and under conditions sufficient to effect its activity.

Another aspect of the present invention is directed to a pharmaceutical composition useful in reducing, inhibiting or preventing ocular inflammation in a mammal comprising an effective amount of matrine or a derivative thereof and a pharmaceutically acceptable carrier.

Yet another aspect of the present invention contemplates a method of inducing ocular analgesia and a pharmaceutical composition useful for same.

DETAILED DESCRIPTION OF THE INVENTION

Figure 1:
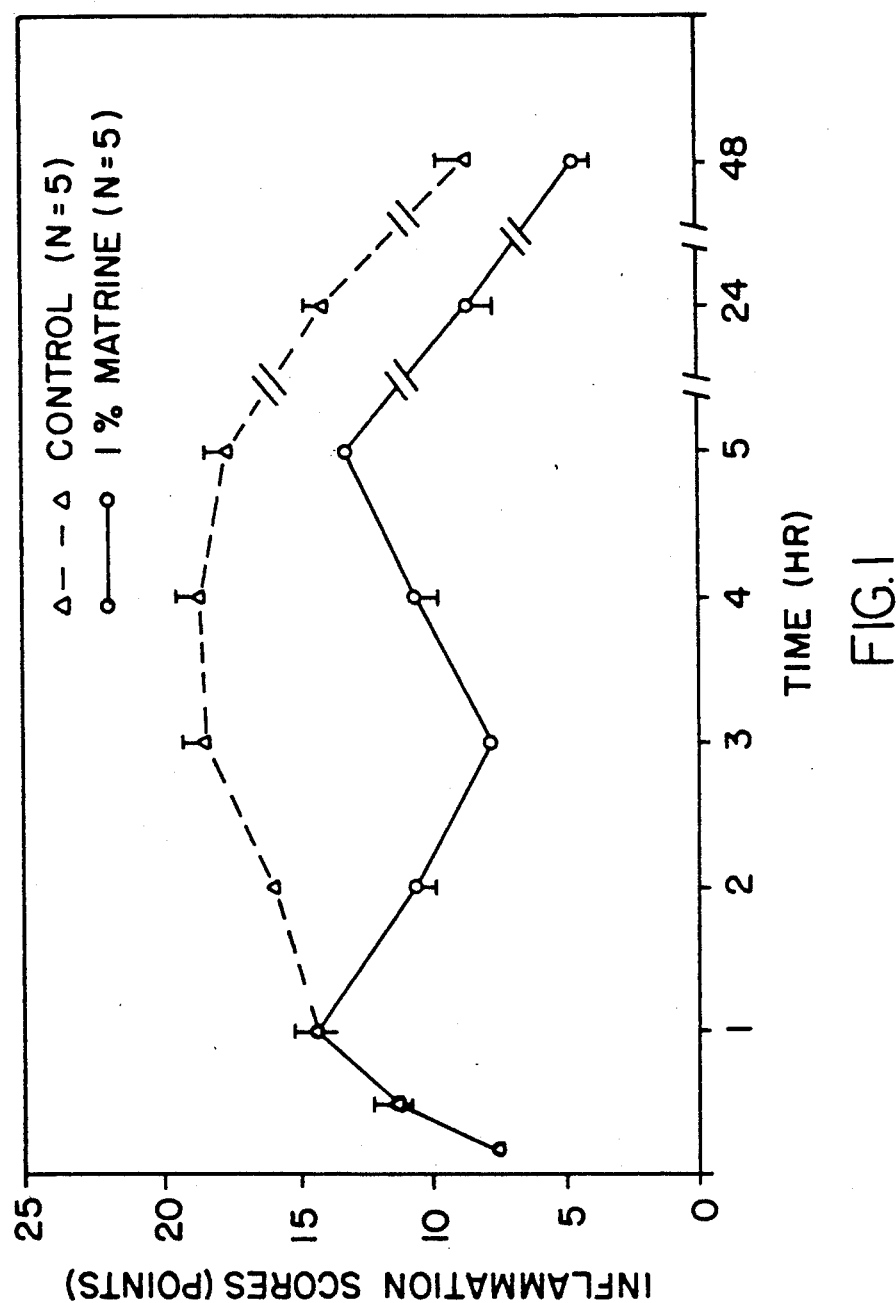
FIG. 1 is a graphical representation showing the effect of topical matrine on ocular inflammation induced by lens protein.

Matrine is an alkaloid ($C_{15}H_{24}NO_2$) natural product obtained from the root of *Sophora subprostrata* (Leguminosae) and has been used in Chinese folk medicine for a variety of conditions including inflammation. In accordance with the present invention, it is surprisingly discovered that administration of matrine reduces, inhibits and/or prevents ocular inflammation. As exemplified herein, matrine, at a concentration of from about 0.1 to about 5 mg per eye, markedly inhibits ocular inflammation. The antiinflammatory action of matrine becomes apparent at from about 1 to about 3 hr after drug administration and peaks at from about 2 to about 4 hr. Ideally, the antiinflammatory action is first detected after about 2 hr and peaks at about 3 hr. As used in the specification and claims herein, matrine encompasses the natural product as well as the synthetic and naturally occurring chemical derivatives and analogs thereof. Derivatives of matrine contemplated by the present invention include alkyl (e.g. methyl, ethyl), substituted alkyl, alkenyl, substituted alkenyl, acyl, dienyl, arylalkyl, arylalkenyl, aryl, substituted aryl, heterocyclic, substituted heterocyclic, cycloalkyl, substituted cycloalkyl, halo (e.g. Cl, Br, I, Fl), haloalkyl, hydroxy, thiol, sulfonyl, carboxy, alkoxy, aryloxy and alkylaryloxy and the like as would be apparent to one skilled in the art. By alkyl, substituted alkyl, alkenyl and substituted alkenyl and the like is meant to encompass lower ($C_1$-$C_6$) and higher (more than $C_6$) derivatives. The present invention is described herein using the natural product, which, up to the present time, represents the best mode of carrying out the present invention. This is done with the understanding that all such synthetic and naturally occurring derivatives of matrine, such as those listed above and as will be apparent to the skilled artisan are encompassed by the present invention. Hereinafter, "derivatives" is used to describe all said synthetic and naturally occurring chemical derivatives and analogs of matrine.

Of the many advantages of the present invention described herein, it is further surprisingly discovered that, unlike corticosteroids, matrine does not facilitate intraocular pressure (IOP) recovery in eyes. In fact, matrine causes a slight delay in IOP recovery indicating that the IOP is lowered rather than increased by matrine. Another advantage of the present invention is the discovery that matrine does not significantly affect systolic blood pressure, diastolic pressure or heart rate. Additionally, in a rabbit model, matrine does not change the electrical potential difference across rabbit iris-ciliary body. As used herein, "activity" of matrine refers to its ability to reduce, inhibit or prevent ocular inflammation or to act as an analgesic.

The present invention is also directed to a pharmaceutical composition comprising matrine. The active ingredients of the pharmaceutical composition exhibit excellent and therapeutic activity, particularly directed to the treatment of ocular inflammation. Thus, the active ingredients of the therapeutic compositions prevent, inhibit or reduce ocular inflammation when topically administered in amounts from about 0.1 mg to about 5.0 mg of matrine per eye. For convenience, solutions can be prepared containing from about 0.1% (w/v) to about 20% (w/v) and preferably 0.5% (w/v) to about 5% (w/v) matrine. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as topically, or by intraocular or intraperitoneal injection. Topical administration includes eye drops, rinses and the like.

The pharmaceutical forms suitable for injectable use include sterile aqueous solutions or dispersions and sterile powders for extremporaneous preparation of sterile injectable solutions or dispersions. In all cases the injectable form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water ethanol, polyol (for example, glycerol, propylene glycol, and liquid polyethylene glycol, and the like) suitable mixtures thereof, and vegetable oils. The proper fluidity can be maintained, for example, by the use of a coating such as licithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thirmersol, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersions media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.1 mg to 5 mg per eye when administered topically or by intraocular injection. Expressed in proportions, the active compound is generally present in from about 1.0 mg to about 200 mg/ml of carrier. When administered intraperitoneally, doses of from about 65 mg/kg to about 200 mg/kg are given and preferably at about 75 mg/kg of body weight. In the case of compositions containing supplementary active ingredients, the dosages are determined by reference to the usual dose and manner of administration of said ingredients.

Another advantage of the present invention is the surprising discovery that matrine has an ocular analgesic effect. This is particularly useful to treat the stinging side effects of other drugs, especially relative to the treatment of ocular inflammation. It is also useful in easing the discomfort of ocular treatment. As exemplified herein, matrine is effective as an ocular analgesic when administered as hereinbefore disclosed. Accordingly, the scope of the present invention encompasses the use of pharmaceutical compositions comprising matrine and a pharmaceutically acceptable carrier in the treatment of ocular inflammation and/or as an analgesic.

When matrine is used for analgesic purposes, the pharmaceutical composition is prepared as disclosed hereinbefore and is administered by a variety of advantageous roots such as topically, intravenous, intramuscular, intranasal, intraperitoneal or intradermal. For administration of the active compound by parenteral and intraperitoneal routes, dispersions can also be prepared in glycerol, liquid polyethylene glycols and mixtures thereof and in oils. Under ordinary conditions of storage and use, these preparations contain a preservative to prevent the growth of microorganisms.

In accordance with the present invention as disclosed herein, matrine is an effective ocular antiinflammatory agent with out serious side effects and has the further advantage of being an ocular mild analgesic.

The present invention is further illustrated by the following examples.

EXAMPLE 1

MATERIALS AND METHODS

Matrine

Matrine is isolated from the root of *Sophora subprostrata* by the method according to Cho et al. *Planta Medica* 5:343-345, 1986, and dissolved in normal saline. Control experiments described herein are done with a corresponding vehicle.

Ocular Inflammation

Ocular inflammation is induced by the administration of lens proteins into the anterior chamber of albino rabbit eyes and graded with the method according to Miyano et al. *Ophth. Res* 16:256-263, 1984. Briefly, 25 ul of rabbit lens protein solution containing 23.72 mg/ml of protein is injected into anterior chamber of the rabbit eye. Ocular inflammation is measured with a slit lamp biomicroscope (Macro, Jacksonville, Florida, USA) at 1/6, ½, 1, 2, 3, 4, 5, 24 and 48 hrs after lens protein injection. Animals are treated with 50 ul of 1% (w/v) matrine topically or with vehicle 1 hr before lens protein injection.

Rabbit IOP Recovery

Rabbit intraocular pressure (IOP) recovery method used is as described by Vareilles et al. *Ophth. Res.* 13:72-79, 1981. Albino rabbits, 2.5-3.0 kg, are infused with 20% (w/v) NaCl solution through a marginal ear vein at a rate of 1 ml/min for 10 min. The IOP is measured with an electronic applanation tonometer (Alcon Labs, Forth Worth, Texas, USA) at $-10$, 0, 10, 20, 40, 60, 80 min and every 30 min thereafter until complete recovery of IOP to the original control value. The IOP measured right before infusion of hypertonic saline is considered 100%. Each animal is used twice, once for a control experiment without drug or vehicle and again 1 week later with 50 ul 1% (w/v) matrine in one eye and vehicle in the other.

Electrical Properties Across Rabbit Iris Ciliary Body

Adult female albino rabbits weights 3-4 kg are sacrificed with overdose pentobarbital sodium injected into the marginal ear vein. The eye is promptly enucleated and mounted between two Lucite chambers using a procedure described by Burstein et al. *Exp. Eye Res,* 39:771-779, 1984.

The basic salt solution (BSS) used contained the following ingredients (mM): NaCl, 110; $NaHCO_3$, 3.8; $KH_2PO_4$, 1.0; $MgSO_4$, 0.86; $CaCl_2$, 1.7; and glucose, 6.9. Each side of the chamber is filled with 10 ml of the bathing solution bubbled with 95% $O_2$ - 5% $CO_2$ at 37° C.

For the measurement of trans-epithelial electrical potential difference, calomel electrodes filled with 3 M KCl are connected to agar bridges filled with 4% (w/w) agar in 5% (w/v) saline. The bridges consisted of PE-200 tubing with one end immersed in the funnels of the tissue chamber. Small electrical asymmetries are nullified with an adjustable series battery. During the experiments both electrodes are temporarily immersed in the same side of the experimental chamber to adjust the battery. Potential difference (PD) is measured with a Keighley electrometer (Model 610C). A permanent record is made by a chart recorder.

Blood Pressure and Heart Rate

New Zealand white female rabbits weighing 3.0-3.5 kg are anesthetized with 30 mg/kg i.v. of pentobarbital sodium. One hour later and throughout the experiment the animal is infused with 12 mg/ml/hr of pentobarbital sodium and 7 mg/ml/hr of decamethonium bromide so that the skeletal muscle is sufficiently immobilized. The femoral artery and vein are cannulated for monitoring systemic blood pressure (RP-1500 Pressure and Model IVA Physiograph, Narco Biosystems, Houston, Texas, USA) and for infusion of the anesthetic and the muscle relaxant. Heart rates counted directly from the pulse tracings of the blood pressure recordings. Fifty microliters of 1% (w/v) matrine instilled to the eye at time zero. Control experiments are done by instilling the same volume of the vehicle. The experiment is run for at least 60 min after drug administration and readings of systemic blood pressure and heart rate are taken at 15 min intervals.

Analgesic Activity

The reaction time of a mouse placed on a hot plate at 55° C.±0.5° C. is used as a means of evaluating analgesic activity according to Eddy et al. *J. Pharmacol. Exp. Ther.* 107:385-393, 1953; and Domer, *Animal Experiments in Pharmacological Analysis*, C. C. Thomas Publisher, Springfield, Illinois, USA pp. 283-284, 1971. Female ICR mice weighing 18-20 g are used. All mice reacted to lick hind paws in about 30 sec. They are tested every 15 min for the first hour and then every 60 min for the following 2 hrs after the administration of matrine (50, 75, 100 mg/kg i.p.).

Statistical Analysis of Data

All data are analyzed with Student's t-test or analysis of variance. Each value is expressed as mean ± standard error of the mean. A p value of 0.05 or less is considered significant.

EXAMPLE 2

Effect of Topical Matrine on Ocular Inflammation

Topical administration of 1% (w/v) matrine markedly inhibits ocular inflammation induced by lens proteins as shown in FIG. 1. Each point in FIG. 1 is a mean value of 5 values and the bars represent SEM. The antiinflammatory action of matrine becomes apparent at 2 hr after drug administration and peaks at 3 hr. Furthermore, at 48 hr, the inflammation is still significantly less than the control.

Figure 2:
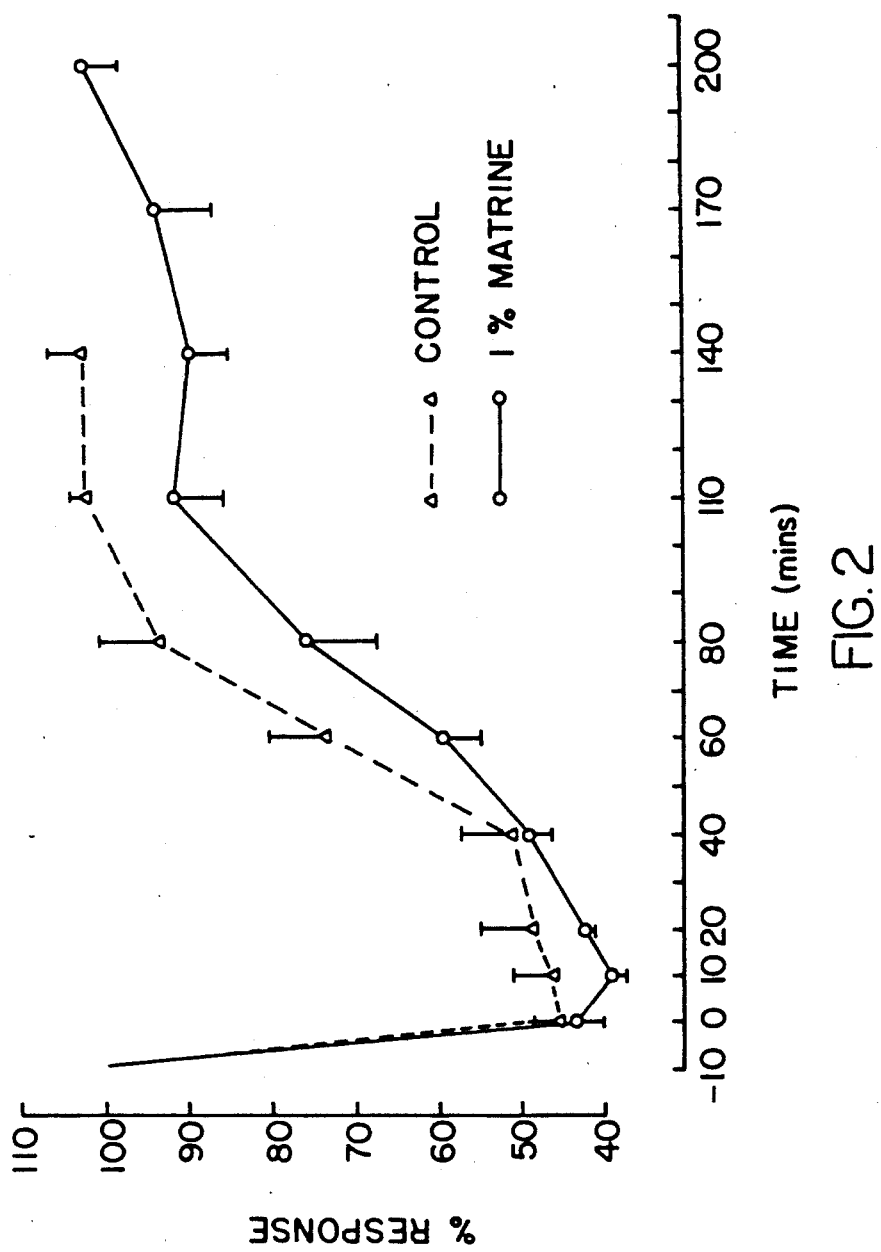
FIG. 2 is a graphical representation showing the effect of topical matrine on rabbit IOP recovery model.

FIG. 2 shows the effect of topical 1% (w/v) matrine on rabbit IOP recovery model. Each point therein is a means of 4 values and bars represent SEM. Unlike corticosteroids, matrine did not facilitate the IOP recovery in rabbit eyes. If any, there is a slight delay of IOP recovery, indicating that IOP is lowered rather than increased with matrine.

Figure 3:
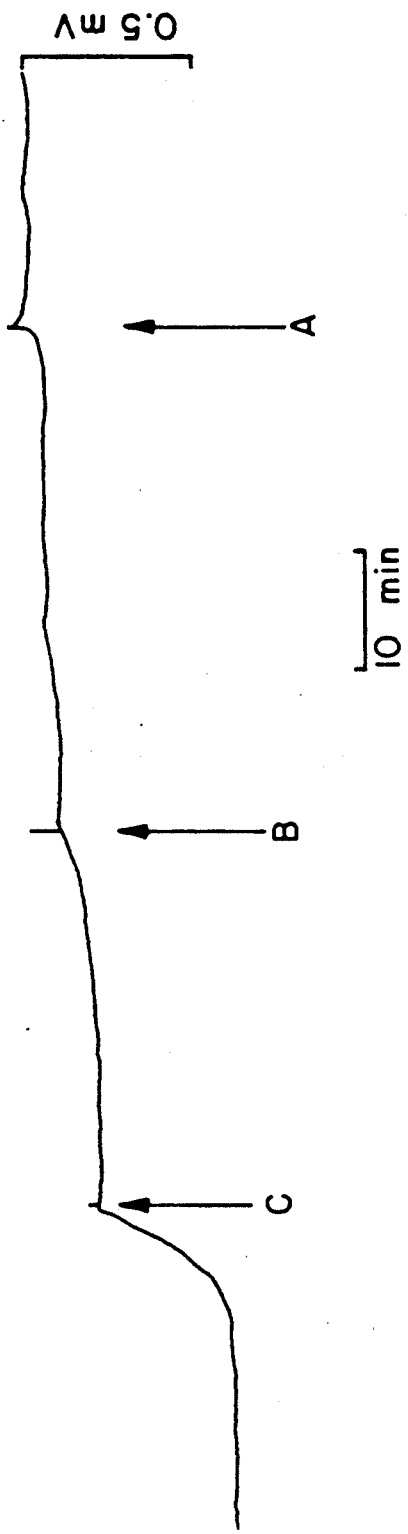
FIG. 3 is a graphical representation showing the effects of matrine and ouabain on PD of isolated rabbit iris-ciliary body preparation.

The inability of matrine to markedly alter the IOP is further confirmed by the fact that matrine (up to $1\times10^{-3}$M) did not affect PD determined in isolated iris-ciliary body chambers (FIG. 3). Since aqueous humor formation is affected by ion transport across ciliary epithelium, any changes in PD measured would indicate a change in aqueous humor formation and subsequently the IOP.

In FIG. 3, A refers to $10^{-3}$M matrine added to the aqueous humor side; B refers to $10^{-3}$ M matrine added in blood side, and C refers to $10^{-5}$ M ouabain. Accordingly, a significant reduction of PD is observed with ouabain but not by matrine.

No significant change is observed by 50 ul 1% (w/w) matrine on systolic blood pressure (77±5 mmHg control vs 75±4 mmHg treated, N=7) and heart rate (230±12 beats/min control vs 223±10 beats/min treated, N=7).

EXAMPLE 3

Analgesic Effects of Matrine on Mice

No analgesic effect by matrine is observed at a dose level of 50 mg/kg i.p. At 75 mg/kg, however, matrine significantly prolongs the reaction time at 15, 30 and 45 min after drug administration. At 100 mg/kg, matrine prolongs even more markedly the reaction time. In some cases, the reaction time lasts beyond 120 sec but the experiments were stopped at 120 sec (Table 1).

TABLE 1

ANALGESIC EFFECTS OF MATRINE ON MICE

| Matrine dose mg/kg | 0 min (Control) | 15 min | 30 min | 45 min | 60 min | 120 min | 180 min |
|---|---|---|---|---|---|---|---|
| 50 | 35.7 ± 3.7 | 42.0 ± 6.9 | 24.8 ± 0.9 | 26.8 ± 2.3 | 32.8 ± 1.8 | 26.8 ± 2.0 | 32.8 ± 2.7 |
| 75 | 34.1 ± 3.3 | 89.2 ± 11.0 | 72.9 ± 7.4 | 56.5 ± 9.2 | 42.6 ± 3.7 | 41.2 ± 4.2 | 41.7 ± 4.5 |
| 100 | 31.6 ± 2.4 | 109.3 ± 10.7 | 95.7 ± 11.4 | 58.7 ± 12.3 | 43.3 ± 13.0 | 44.4 ± 13.0 | 35.7 ± 2.7 | a, Mean ± SEM (N = 7) reaction time (sec) of mice placed on hot plate at 55° ± 0.5° C. to lick hind paws.
b, Statistically different from corresponding control at P <0.05.
c, Some mice had reaction time lasted 120 sec and beyond.

What is claimed is:

1. A method of reducing, inhibiting or preventing ocular inflammation in a mammal in need of such treatment which comprises administering to said mammal an amount of matrine or a derivative thereof for a time and under conditions effective to reduce, inhibit or prevent ocular inflammation.

2. The method according to claim 1 wherein said mammal is selected from the group consisting of human and rabbit.

3. The method according to claim 1 wherein matrine or its derivative is provided by topical or intraocular administration.

4. The method according to claim 1 wherein the effective amount is about 0.1 mg to about 5 mg per eye.

5. The method according to claim 1 wherein the derivative of matrine is an alkyl or substituted alkyl derivative.

6. The method according to claim 1 wherein the derivative of matrine is an alkenyl derivative.

7. The method according to claim 1 wherein the derivative of matrine is an aryl derivative.

8. The method according to claim 1 wherein the derivative of matrine is an arylalkyl or arylalkenyl derivative.

9. The method according to claim 1 wherein the derivative of matrine is a cycloalkyl derivative.

10. The method according to claim 1 wherein the derivative of matrine is a halo or haloalkyl derivative.

11. The method according to claim 1 wherein the derivative of matrine is a hydroxy derivative.

12. The method according to claim 1 wherein derivative of matrine is a thiol or sulfonyl derivative.

13. The method according to claim 1 wherein the derivative of matrine is a carboxy or alkoxy derivative.

14. The method according to claim 1 wherein the derivative of matrine is an aryloxy or alkylaryloxy derivative.

15. The method according to claim 1 wherein the derivative of matrine is a dienyl derivative.

16. A method of inducing ocular analgesia in a mammal in need of such treatment which comprises administering to said mammal an amount of matrine or a derivative thereof for a time and under conditions effective to induce ocular analgesia.

17. The method according to claim 16 wherein said mammal is a human.

18. The method according to claim 16 wherein the induction of analgesia is effected by topical, intraocular, intravenous, intramuscular, intranasal, intradermal or intraperitoneal administration.

19. The method according to claim 16 wherein the effective amount is from about 0.1 mg to about 5.0 mg per eye.

* * * * *